United States Patent
Chodorge et al.

(10) Patent No.: US 7,983,849 B2
(45) Date of Patent: Jul. 19, 2011

(54) METHOD OF DETERMINING THE MUTATIONAL LOAD OF A GENE LIBRARY OBTAINED BY RANDOM MUTAGENESIS OF A PARTICULAR GENE AND MEANS FOR IMPLEMENTING SAME

(75) Inventors: Matthieu Chodorge, Antony (FR); Laurent Fourage, Clarensac (FR); Fabrice Lefevre, Bajonnette (FR); Jean-Michel Masson, Toulouse (FR)

(73) Assignee: Proteus S.A., Nimes (FR)

( * ) Notice: Subject to any disclaimer, the term of this patent is extended or adjusted under 35 U.S.C. 154(b) by 1110 days.

(21) Appl. No.: 11/628,763

(22) PCT Filed: Jun. 7, 2005

(86) PCT No.: PCT/FR2005/001392
§ 371 (c)(1),
(2), (4) Date: May 4, 2007

(87) PCT Pub. No.: WO2006/003298
PCT Pub. Date: Jan. 12, 2006

(65) Prior Publication Data
US 2008/0139397 A1    Jun. 12, 2008

(30) Foreign Application Priority Data
Jun. 7, 2004 (FR) .................................... 04 06120

(51) Int. Cl.
*G01N 33/50* (2006.01)
(52) U.S. Cl. ........................................ 702/19; 536/25.3
(58) Field of Classification Search .................. None
See application file for complete search history.

(56) References Cited

U.S. PATENT DOCUMENTS
2001/0037454 A1* 11/2001 Botti et al. .................... 713/176
2003/0152944 A1* 8/2003 Hogrefe et al. .................... 435/6

OTHER PUBLICATIONS

Patrick et al. (Protein Engineering, vol. 16, No. 6, p. 451-457, Jun. 2003).*
Vu et al. (Nucleic acids research, vol. 28, No. 7, e18, pp. 9, 2000).*
Cirino et al. (From: Methods in Molecular Biology, vol. 231: Directed Evolution Library Creation: Methods and Protocols Edited by: F. H. Arnold and G. Georgiou O, Humana Press Inc., Totowa, NJ, p. 3-9, 2003).*
Wilson et al.( Current Protocols in Molecular Biology (2000) 8.3.1-8.3.9 Copyright © 2000 by John Wiley & Sons, Inc.).*

* cited by examiner

*Primary Examiner* — Karlheinz R Skowronek
(74) *Attorney, Agent, or Firm* — Hunton and Williams, LLP

(57) ABSTRACT

The invention relates to methods of determining the mutational load of a gene bank obtained by random mutagenesis of a gene of interest by preparing a chart linking the mutational load of a gene bank obtained by random mutagenesis of a model gene with the fraction of mutated model genes observed in the bank; performing, in parallel, random mutagenesis of the model gene used for preparing the chart and the gene of interest to obtain the corresponding mutated gene banks; determining the mutational load of the gene bank obtained using the model gene on the basis of the chart plotted; and applying a correction factor to the mutational load of the mutated model gene bank to determine the mutational load in the gene bank of the mutated genes of interest.

29 Claims, 6 Drawing Sheets

Figure 1

```
1    tttcaagagtgccatgcccgagggttatgtacaggaaagaactatattttcaaagatga   60
61   cgggaactacaagacacgtgctgaagtcaagtttgaaggtgatacccttgttaatagaat  120
121  cgagttaaaaggtgttgattttaaagaagatggaaacattcttggacacaaattggaata  180
181  caactataactcacacaatgtatacatcatggcagacaaacaaaagaatggaatcaaagc  240
241  taacttcaaagttagacacaacattgaagatggaagcgttcaactggcagaccattatca  300
301  acaaaatactccaattggcgatggccctgtccttttaccagacaaccattacctgtccac  360
361  acaatctgcccttttcgaaagatcccaacgaaaagagagaccacatggtccttcttgagtt  420
421  tgtaacagctgctgggattacacatggcatggatgaactatacaaataaatgagtaaagg  480
481  agaagaacttttcactagagttgtcccaattcttgttgaattagacggtgatgttaatgg  540
541  gcacaaattttctgtcagtggagagggagaaggtgatgcaacatacggaaaacttaccct  600
601  taaatttatttgcactactggaaaactaccagttccgtggccaacacttgtcactactct  660
661  ctcttatggtgttcaatgcttttcgagatacccagatcacatgaaacggcatgactt     717
```

Figure 4

Target gfp matrix
for PCRep

| | |
|---|---|
| A | 0.506 |
| T | 0.346 |
| C | 0.063 |
| G | 0.085 |

SEQUENCE LISTING

<160> NUMBER OF SEQ ID NOS: 1

<210> SEQ ID NO 1
<211> LENGTH: 717
<212> TYPE: DNA
<213> ORGANISM: Aequorea victoria

<400> SEQUENCE: 1

```
tttcaagagt gccatgcccg agggttatgt acaggaaaga actatatttt tcaaagatga        60
cgggaactac aagacacgtg ctgaagtcaa gtttgaaggt gatacccttg ttaatagaat       120
cgagttaaaa ggtgttgatt ttaaagaaga tggaaacatt cttggacaca aattggaata       180
caactataac tcacacaatg tatacatcat ggcagacaaa caaaagaatg gaatcaaagc       240
taacttcaaa gttagacaca acattgaaga tggaagcgtt caactggcag accattatca       300
acaaaatact ccaattggcg atggccctgt ccttttacca gacaaccatt acctgtccac       360
acaatctgcc ctttcgaaag atcccaacga aaagagagac cacatggtcc ttcttgagtt       420
tgtaacagct gctgggatta cacatggcat ggatgaacta tacaaataaa tgagtaaagg       480
agaagaactt ttcactagag ttgtcccaat tcttgttgaa ttagacggtg atgttaatgg       540
gcacaaattt tctgtcagtg gagagggaga aggtgatgca acatacggaa aacttaccct       600
taaatttatt tgcactactg gaaaactacc agttccgtgg ccaacacttg tcactactct       660
ctcttatggt gttcaatgct tttcgagata cccagatcac atgaaacggc atgactt         717
```

METHOD OF DETERMINING THE MUTATIONAL LOAD OF A GENE LIBRARY OBTAINED BY RANDOM MUTAGENESIS OF A PARTICULAR GENE AND MEANS FOR IMPLEMENTING SAME

This application is the national phase of International Application No. PCT/FR2005/001392, filed Jun. 7, 2005, which claims priority to French Patent Application No. FR 0406120, filed Jun. 7, 2004.

The present invention relates to a method used to determine the mutational load introduced into a gene bank following a random mutagenesis step of a gene of interest. The invention also relates to the means for the use of this method such as kits and media intended for to be processed by computers.

Random nucleic acid mutagenesis makes it possible to introduce modifications into protein amino acid sequences. It consists of an effective alternative strategy to directed mutagenesis and rational protein design. In fact, in the absence of any precise data on the characteristics of a protein such as its structure, i.e. in the majority of cases, only random mutagenesis makes it possible to identify mutants or variants of a gene that have acquired new properties rapidly.

As a general rule, although it has been possible to isolate improved variants in hyper-mutated banks (Zaccolo M. et al. (1999) Journal of Molecular Biology. 285:775-783), it is acknowledged that the introduction of an excessively high number of mutations results in a majority of inactive proteins and limits the identification of enhanced variants severely while an excessively low mutation rate decreases the likelihood of obtaining beneficial mutation. In this way, several examples of directed evolution would tend to demonstrate that the most effective mutation rate to identify improved variants would be 1-5 amino acids per protein, i.e. 2-7 nucleotides per gene (Cherry J. R. et al. (1999) Nature Biotechnology. 17:379-384./Shafikhani S. et al. (1997) BioTechniquers 23:304-310./Moore J. C. et al. (1997) Journal of Molecular Biology. 272:336-347.)

Therefore, it is necessary to be able to control the number of mutations introduced into a gene bank by random mutagenesis. The mutational load (ML) is defined as the mean number of mutations per gene in a mutated gene bank.

The reference method of the prior art to determine the mutation rate accurately in a mutated gene bank still remains statistical observation by sequencing a fraction of genes from the bank. This method remains complex to implement and above all very costly.

As an alternative to sequencing, other methods to quantify the mutation rate have been developed such as "Single Strand Conformation Polymorphism" (SSCP) or "Denaturing Gradient Gel Electrophoresis" (DGGE) which are used to detect differences between sequences up to a base (Cariello et al. (1993) Mutational Research 288:103-112/Brail et al, (1993) Mutational Research 303:171-175). However, these techniques are more suitable for a qualitative analysis such as the detection of mutation and the determination of low error rates than for a quantification of mutational load.

Another method according to the prior art makes use of the analysis of changes in the restriction profile of sequences having integrated or lost specific restriction sites. Therefore, this method is only applicable to specific sequences with a modification of representative restriction sites.

A method to monitor the mutation frequency based on phenotypic tests in which a reporting gene undergoes random mutagenesis before cloning has also been proposed. In this case, the mutation frequencies are simply analysed by recording the loss of functionality of the reporting gene product due to the appearance of mutations therein. However, this method is limited to genes for which the introduction of mutations can be observed easily by means of a phenotypic test. Tables used to associate a mutational load of mutated gene bank for a given gene of interest with experimental conditions according to its length have also been described in the prior art. These tables are constructed on the basis of a model gene subjected to various experimental conditions followed by the sequencing of a statistically representative number of genes from the mutated gene bank. However, these techniques only account for the length of said gene of interest.

In addition, none of the methods according to the prior art use an internal standard making it possible to account for experimental variabilities liable to influence the mutational load of a bank. This means that these methods are not sufficiently reliable and reproducible for it to be possible to do away with sequencing in order to determine the mutational load obtained in a mutated gene bank.

The purpose of the present invention is specifically to offer, in the field of random mutagenesis, reliable methods for the prediction of the mutational load of mutated gene banks.

This aim is achieved according to the invention by means of a method to determine the mutational load of a gene bank obtained by means of random mutagenesis of a gene of interest, characterised in that it comprises the following steps:

a) the preparation of a chart linking the mutational load (ML) of a gene bank obtained by means of random mutagenesis of a model gene with the fraction of mutated model genes observed in said bank;

b) the random mutagenesis of the model gene used for the preparation of the chart for step (a) and the gene of interest to obtain the corresponding mutated gene banks;

c) the determination of the mutational load (ML) of the gene bank obtained using the model gene in step (b) on the basis of the chart plotted in step (a);

d) the application of a correction factor (CF) to the mutational load (ML) of the mutated model gene bank determined in step (c) to determine the mutational load (ML) of the banks of mutated genes of interest from step (b).

According to a preferential embodiment of the method according to the invention, the mutagenesis technique used in step (b) is identical for the model gene and for the gene of interest and is also similar to that of step (a) to construct the chart on the basis of the model gene. Advantageously, the term identical or similar technique refers to the fact that not only is the technique the same, but also the conditions of use. The similarity or identity of the mutagenesis technique and its conditions do not exclude the fact that those skilled in the art may make adaptations which are not of a nature to substantially modify the performances of the mutagenesis technique. For example, the polymerases used in steps (a) and (b) to implement a PCR error-prone technique may not be identical.

Similarly, those skilled in the art are able to determine a different model gene for step b) to that of step a), but displaying substantially equivalent properties for the implementation of said steps.

The method according to the invention is characterised in that it offers sufficient accuracy to represent an effective alternative to sequencing which is very costly. In this way, steps (c) and (d) may do away with sequencing.

In the subsequent description of the invention below, the following terms are used indifferently:

"gene bank obtained by means of random mutagenesis of a model gene" or "mutated model gene bank"; and "gene bank obtained by means of random mutagenesis of a gene of interest" or "mutated gene of interest bank"

The term gene used in the sense of the present invention refers to any nucleotide acid sequence, coding or not.

An essential characteristic of the present invention lies in the fact that the modifications of the model gene sequence can be observed after mutagenesis.

The term mutated model genes refers to model genes wherein the nucleotide sequence is modified with respect to that of the model gene before mutagenesis.

The term observed mutated model gene refers to a model gene wherein the sequence modification is observable.

The term observable refers to the fact that the random introduction of mutation is not analysed by sequencing but by the direct or indirect analysis of the modification of one or more properties of the mutated model genes with respect to the model gene before mutagenesis.

The term indirect analysis refers to the fact that the modification of one or more properties of the mutated gene is observed by means of intermediate reaction.

For example, the modification of a model gene may be observed by means of the modification of one or more properties of the protein coded by the model gene. The modification of one or more properties of the protein may consist of the loss or gain in activity/activities characterising the protein.

In a preferred embodiment of the invention, the mutated model genes are observed by means of a phenotypic test. The term phenotypic test refers to a test used to detect the function of the protein coded by the model gene, mutated or not.

Examples of genes wherein the function can be detected by means of a phenotypic test include those:
  involved in antibiotic resistances,
  involved in host strain auxotrophy,
  coding for a protein displaying an easily detectable activity (beta-galactosidase/xylanase/Green Fluorescent Protein (GFP . . . ),
  coding for a protein involved in an antigen-antibody type immunological reaction.

The model gene is used in the method according to the invention to:
  plot a chart as defined in step (a), and
  be used in parallel with the gene of interest in step (b) to account for the variabilities that the experimental conditions are liable to cause on random mutagenesis results, and thus serve as an internal standard.

Unlike a reference conventionally used in biology, the internal standard defined in the method according to the invention by the model gene does not only indicate the satisfactory completion or the degree of progress of an experiment, it also gives a measurement required to carry out the method.

In one particular embodiment of the invention, the model gene is a so-called universal model gene, i.e. it has characteristics shared by a large number of genes. For example, it displays a length between 500 pb and 10 kpb and a GC percentage between 20 and 80. Preferentially, the universal model gene displays a GC percentage between 40 and 60. An example of a universal model gene includes the gene coding for GFP protein, wherein the introduction of mutations can be carried out by means of a phenotypic test whereby the ultraviolet fluorescence of the colonies reflects an active GFP phenotype.

In another preferred embodiment of the invention, the model gene displays similar characteristics to those of the gene of interest. These characteristics correspond advantageously to intrinsic properties. The term intrinsic properties of a gene refers to the properties inherent to the sequence of said gene.

Non-limitative examples of the intrinsic properties of a gene envisaged above include:
  its length,
  its base composition, the base composition may be advantageously analysed on a single strand,
  its frequency of bases repeated in the sequence,
  the presence of symmetric sequences in the gene.

Once the model gene has been selected, a random mutagenesis technique is selected to implement the method according to the invention. The term random mutagenesis technique refers to any technique known to those skilled in the art. It may also correspond to a combination of several mutagenesis techniques. It may be in vivo or in vitro.

In one preferred embodiment, the method according to the invention relates to in vitro mutagenesis techniques based preferentially on the use of a polymerase or on the use of an amplification technique. For example, the mutagenesis technique corresponds to error-prone PCR (Cadwell R. C et al. (1992) PCR Methods Appl. 2:28-33./Leung D. W. et al. (1989) Techniques 1:11-15.)

Once the model gene has been selected and the mutagenesis technique chosen, a chart used to associate the gene bank obtained by means of random mutagenesis of a model gene with the fraction of mutated model genes observed in said bank is prepared (step a).

The term chart according to the invention refers to any graph, table or equation making it possible to associate the mutational load (ML) of a gene bank obtained by means of random mutagenesis of a model gene in a one-to-one manner with the fraction of mutated model genes observed in said bank.

A chart is obtained for a mutagenesis technique and a given model gene.

In this way, in the preferred embodiment of the invention wherein the modification of the model gene can be observed by means of a phenotypic test, the chart obtained in step (a) makes it possible to associate the mutational load of a gene bank obtained by means of random mutagenesis of the model gene with the fraction of genes displaying a mutant phenotype in said bank.

The chart may have been produced previously by those skilled in the art or may be obtained as follows:
  i) A given mutagenesis technique is applied to a previously selected model gene to obtain a mutated model gene bank.
  ii) The mutational load (ML) in the mutated model gene bank is then determined by sequencing. The fraction of mutated model genes in said bank displaying a modification of one or more properties with respect to the wild gene is observed in parallel.

In one preferred embodiment of the invention, a statistically representative number of clones is analysed and the corresponding mutated model gene is sequenced. In one preferred embodiment of the invention, between 10 and 100 clones are sequenced. Advantageously, the sequencing is performed on 25 clones while the analysis of the clone fraction displaying a sequence modification is performed on at least 500 clones.

A one-to-one link can thus be established between the mutational load of a gene bank obtained by means of random mutagenesis of a model gene and the fraction of mutated model genes observed in said bank.

With this chart, the random mutagenesis technique used to construct the chart is applied in parallel with the model gene and with a gene of interest in step (b), the model gene of step (b) being preferentially the same as that used to construct the chart in step (a).

In step (b), the same mutagenesis technique is applied simultaneously to the model gene and to the gene of interest.

Using the model gene with the gene or interest in step (b) is equivalent to using the model gene as an internal standard. Using the model gene as an internal standard offers the advantage:
- of accounting for the experimental variations liable to occur during an experiment performed in step (b) on the model gene with respect to those performed previously to obtain the relationship defined in step (a);
- of minimising the experimental variations between samples, i.e. of the processing of the model gene with respect to the gene of interest during step (b).

These experimental variations are non-negligible on the mutational load observed. In fact, it has been demonstrated that even minimal modifications of the experimental conditions are liable to have significant consequences on the mutational load introduced into a bank. Table 1 below gives the means, standard deviations and coefficients of variation C.V. (C.V.=standard deviation/mean as a %) of the clone fractions expressing a functional GFP following six repeated error-prone PCR experiments with different concentrations of $MgCl_2$ and $MnCl_2$ (mutagenesis level monitoring parameters). On the basis of an experiment repeated under identical conditions, the result of the error-prone mutagenesis is significantly variable with coefficients of variation on the clone fractions expressing a functional GFP and therefore of the mutation rate between 10 and 40%.

TABLE 1

| Reaction conditions | | Active gfp clone population fraction | | |
|---|---|---|---|---|
| [MgCl2] mM | [MnCl2] mM | Mean | Standard deviation | CV (%) |
| 5 | 0 | 0.722 | 0.071 | 9.9 |
| 7 | 0.2 | 0.411 | 0.122 | 29.7 |
| 7 | 0.4 | 0.091 | 0.040 | 43.8 |
| 7 | 0.5 | 0.036 | 0.013 | 35.5 |

Table 1 above gives the variability of the clone fraction expressing a functional GFP in banks of gfp genes mutated randomly by means of error-prone PCR during experiments repeated 6 times under identical conditions.

Therefore, step (b) is the key step in the method according to the invention. It makes it possible to account for the experimental variations liable to occur during the use of a random mutagenesis technique on a gene of interest, said variations possibly influencing the definition of the mutational load of the gene bank obtained in this way. For this reason, the method according to the invention makes it possible to do away with sequencing in steps (c) and (d) to determine the mutational load of a mutated gene of interest bank.

In one particularly preferred embodiment of the invention, the same reaction mixture is used to implement the mutagenesis technique in parallel on the model gene and on the gene of interest to minimise the experimental variations between samples further.

The mutated model gene bank is then analysed to determine the mutational load of the corresponding bank (step c). After step (b), the fraction of mutated model genes observed in the bank obtained after mutagenesis of the model gene is determined. Using the chart defined in step (a), the fraction of mutated model genes observed in said bank makes it possible to define the mutational load of said bank.

In step (d), the mutational load determined in step (c) is corrected by applying a correction factor (CF) thereto to determine the mutational load introduced into the gene bank obtained by means of random mutagenesis of the gene of interest.

This is performed according to the following equation:

$$ML(\text{gene of interest}) = ML(\text{model gene}) \times CF$$

wherein, CF represents the correction factor and ML represents the mutational load The correction factor (CF) can be broken down into several correction sub-factors according to the parameters selected as influencing the mutational load of a mutated gene of interest bank with respect to a mutated model gene bank.

A correction sub-factor is used to standardise the effect of a parameter selected as capable of influencing the mutational load of one bank with respect to another.

The construction of the correction factor CF is performed by multiplying the different sub-factors that are to be taken into account for the determination of the mutational load of the mutated gene of interest bank in the method according to the invention.

The parameters selected as being liable to influence the mutational load may correspond for example to one or more of the following parameter:
- intrinsic parameters
- experimental parameters.

The term intrinsic parameters of a gene refers to those resulting from the sequence of said gene as described above.

The term experimental parameter refers to any parameter capable of inducing differences in the introduction of mutations in the model gene with respect to the gene of interest during the use of the mutagenesis technique.

The nature of these experimental parameters is dependent on the random mutagenesis technique used. They can only be calculated after implementing the mutagenesis technique on the model gene and on the gene of interest in step (b).

The consideration of this type of parameter to perform the correction in step (d) is added to the advantage of using an internal standard in order to account for experimental variations optimally on the determination of the mutational load of a gene bank.

In the case of mutagenesis techniques based on the use of PCR (including error-prone PCR), the experimental parameters may correspond, in a non-limitative manner:
- to the multiplication number of the gene during the random mutagenesis step,
- to the quantity of initial matrix,
- to the number of amplification cycles,
- to the type and quantity of polymerase used
- to the experimental conditions used such as the divalent cation concentration, the DNTP concentration and concentration ratio.

The various correction sub-factors must be defined according to mathematical laws accounting for the nature of the biological events to be standardised.

For example, it is agreed in the prior art that the number of mutations into a gene is associated linearly with the gene length (intrinsic parameter).

In this way, CF[L], defined as the correction sub-factor associated with the gene length, is explained as follows:

$CF[L] = L(\text{gene of interest})/L(\text{model gene})$ where $L$ corresponds to the gene length.

Similarly, it is known in the prior art that different mutagenesis methods do not affect the various A, T, G or C nucleotides in an equivalent way. For each mutagenesis method, it is possible to define a correction sub-factor CF[base] which accounts for the differences in base composition between the model gene and the gene of interest with respect to the mutation introduction method of the mutagenesis technique.

In order to establish such a correction sub-factor, it is necessary to introduce the concept of a target mutation matrix.

In fact, the target mutation matrix of the model gene (Mtarget[X] where X represents the model gene) breaks down on the four bases the likelihood of encountering a particular type of base in the model gene and is used to standardise the base composition with respect to the model gene used.

The target mutation matrix of the model gene is deduced from sequencing of the mutated model genes by means of a defined random mutagenesis technique and identification of the mutations that occur.

The analysis of the mutations occurring in the mutated model gene sequences makes it possible to define the mutation matrix $Mut_X$, where $Mut_X$ lists the frequencies of the 12 possible types of mutations according to the following matrix:

$$Mut_X = \begin{pmatrix} & f_{A \to T} & f_{A \to C} & f_{A \to G} \\ f_{T \to A} & & f_{T \to C} & f_{A \to G} \\ f_{C \to A} & f_{C \to T} & & f_{C \to G} \\ f_{G \to A} & f_{G \to T} & f_{G \to C} & \end{pmatrix}$$

wherein, $f_{X \to Y}$ represents the probability of mutating base X to base Y.

The target mutation matrix of the model gene X, $M_{target}[X]$ is then deduced from the matrix $Mut_X$ by adding the three frequencies affecting a type of base according to the following matrix:

$$M_{target}[X] = \begin{pmatrix} A_{Mtarg[X]} \\ T_{Mtarg[X]} \\ C_{Mtarg[X]} \\ G_{Mtarg[X]} \end{pmatrix}$$

wherein, $$Z_{Mtarg[X]} = \sum_{Y=(A,T,C,G)-Z} f_{Z \to Y},$$

where Z is A, T, C or G.

The target mutation matrix is dependent on the nature of the model gene. The richer a model gene is in a particular type of base, the higher the likelihood of this type of base being affected with a defined random mutagenesis method.

The target mutation matrix is dependent on the mutagenesis technique used as it depends on the bias of the random mutagenesis method.

In this way, CF[base], defined as the correction sub-factor associated with the base composition, is explained according to the following equation:

$$C.F. [base] = \left( \frac{AMtarg[X] * A(g \cdot interest)}{A(X)} + \frac{TMtarg[X] * T(g \cdot interest)}{T(X)} + \frac{CMtarg[X * C(g \cdot interest)}{C(X)} + \frac{GMtarg[X * G(g \cdot interest)}{G(X)} \right)$$

wherein, $A_{(g.interest)}$, $A_{(X)}$, $T_{(g.interest)}$, $T_{(X)}$, $C_{(g.interest)}$, $C_{(X)}$, $G_{(g.interest)}$ and $G_{(X)}$ correspond respectively to the base A, T, C and G composition of the model gene X and the gene of interest.

In addition, the impact of some mutagens on a given nucleotide may vary significantly depending on the type of nucleotide adjacent thereto in the sequence. For this reason, the corrective factor may incorporate, if relevant, a comparative term between the dinucleotide frequencies in the gene of interest with respect to the model gene.

Similarly, the relative trinucleotide frequency between the model gene and the gene of interest may be taken into account in the corrective factor.

Also for example, in the case of a PCR-based "in vitro" mutagenesis, the multiplication rate (experimental parameters) applied to the matrix will influence the mutation rate directly. In fact, the replication efficiency is dependent on the DNA matrix and the PCR programme used. Due to differences in length, base composition, the presence of secondary structures, some genes are more difficult to amplify than others. In this way, any differences in the PCR yield between the mutagenesis of the model gene and that of the gene of interest may induce differences in the multiplication rate, even using an identical quantity of matrix and performing the same number of PCR cycles. The multiplication rate (d) is calculated according to the following equation:

$$d = \ln(Qf/Qi)/\ln 2$$

wherein, Qi and Qf respectively represent the molar quantities of initial matrix and product following the PCR.

The initial quantity of matrix and final quantity of product may be determined by numerous means known to those skilled in the art. These include for example UV spectrophotometric assays or calibration with respect to known quantity of DNA.

The experimental parameters may also correspond to the number of generations of a cell culture for an "in vivo" mutagenesis technique. For example, in the case of "in vivo" mutagenesis, the number of mutations introduced into the genes will depend on the number of generations of the culture. In this case, the investigator must take care to analyse it, for example by measuring the culture turbidity.

Various embodiments of the invention may be envisaged, where:
at least one intrinsic parameter of each of the model gene and gene of interest is taken into consideration to calculate the correction factor,
at least two intrinsic parameters of the model gene and the gene of interest are taken into consideration to calculate the correction factor according to the following equation:

$$CF = CF[\text{intrinsic parameter 1}] \times CF[\text{intrinsic parameter 2}]$$

For example, these intrinsic parameters correspond to the length and base composition of the genes, according to the following equation:

$$CF = CF[L] \times CF[\text{base}]$$

wherein:
CF[L], the correction sub-factor is associated with the length of the genes,
CF[base], the correction sub-factor is associated with the base composition of the genes,
at least one intrinsic parameter and at least one experimental parameter are taken into consideration to determine the correction factor, where C.F. is determined according to the following equation:

$$CF = CF[\text{intrinsic parameter}] \times CF[\text{experimental parameter}]$$

at least two intrinsic parameters and at least one experimental parameter are taken into consideration to determine the correction factor, where CF is determined according to the following equation:

$$CF=CF[\text{intrinsic parameter 1}] \times CF[\text{intrinsic parameter 2}] \times CF[\text{parameter}]$$

In the specific case wherein the mutagenesis technique corresponds to error-prone PCR and the model gene corresponds to GFP (SEQ ID NO:1), different correction subfactors correspond such that:

intrinsic parameter 1 represents the length of the genes according to the following equation:

$$CF[L]=L(\text{gene of interest})/717$$

where L is expressed in number of base pairs, intrinsic parameter 2 represents the base composition on the DNA strands according to the following equation:

$$C.F. \text{ [base]} = \left( \frac{0.506 \times A_{(g\cdot interest)}}{0.34} + \frac{0.346 \times T_{(g\cdot interest)}}{0.26} + \frac{0.063 \times C_{(g\cdot interest)}}{0.197} + \frac{0.85 \times G_{(g\cdot interest)}}{0.203} \right)$$

where $A_{(g.interest)}$, $T_{(g.interest)}$, $C_{(g.interest)}$ and $G_{(g.interest)}$ are in fractions, experimental parameter represents the multiplication rate according to the following equation:

$$CF[d]=d(\text{gene of interest})/d(gfp)$$

where d is the multiplication rate calculated according to the following equation:

$$d=\ln(Qf/Qi)/\ln 2$$

wherein, Qi and Qf respectively represent the molar quantities of the initial matrix and the products following the PCR.

The invention also relates to the uses of the method defined above:

1) The method according to the invention may be used to obtain and control the desired mutational load in a mutated gene of interest bank. The investigator, on the basis of a chart making it possible to associate the mutational load of a mutated model gene bank with the experimental random mutagenesis conditions, will select the experimental conditions or a range of experimental conditions making it possible to approach a desired mutational load for the bank obtained after random mutagenesis of a gene of interest. The investigator will make this selection by accounting for at least one intrinsic parameter of the model gene and gene of interest. The investigator then implements steps (a) to (d) of the method according to the invention described above using, in step (b), the previously selected experimental conditions. He/she then uses the method according to the invention to verify that the mutational load introduced is indeed that desired. In this way, the use of the method according to the invention to obtain and control a desired mutational load in a mutated gene of interest bank is characterised by the use of an additional step for the selection of the random mutagenesis experimental conditions to be used to implement step (b). For example, this use makes it possible to control the mutational load in a mutated gene of interest bank prior to a structure-function study. The investigator firstly produces a low-mutation gene of interest bank and verifies, by means of the method according to the invention, that the mutational load introduced is indeed 1-2 mutations per gene, the optimal number of mutations for this type of application (Vartanian J. P., Henry M., Wain-Hobson S. Hypermutagenic PCR involving all four transitions and a sizeable proportion of transversions. Nucleic Acids Res. (1996). 24:2627-2631). Screening of variants from the bank in a given function and sequencing of clones identified as positive then make it possible to associate the sequence unambiguously with the function studied.

2) The method according to the invention may be used to control the mutational load in a mutated gene of interest bank prior to screening for enhanced variants. The investigator firstly produces a mutated gene of interest bank and verifies, by means of the method according to the invention, that the mutational load introduced is indeed 3-7 mutations per gene, the optimal number of mutations for this type of application (Wan L. et al. (1998) Proc. Natl. Acad. Sci. USA 95:12825-12831. / You L et al. (1996) Protein Eng. 9:77-83). The application of optimal number of mutations makes it possible to increase the likelihood of identifying genes coding for enhanced proteins.

3) The method according to the invention may be used to study the protein plasticity, i.e. the ability to incorporate mutations while retaining an activity displayed by the wild protein (Shafikhani S. et al. (1997) BioTechniquers 23:304-310). The investigator firstly produces gene of interest banks with varying levels of mutation and then determines, by means of the method according to the invention, the mutational loads associated with the various banks. The analysis of the clone fractions producing a functional protein variant in the various banks makes it possible to study the plasticity of the gene of interest product by associating said banks with the previously determined mutational loads.

4) The method according to the invention may be used to study the rate of evolution of a protein of interest, i.e. the ability to acquire a new property with a given mutational load (Miura T. et al. (2001) J. theor. Biol. 209:497-502). The investigator firstly produces gene of interest banks with varying levels of mutation and then determines, by means of the method according to the invention, the mutational loads associated with the various banks. The analysis of the clone fractions producing a variant displaying an original property with respect to the wild protein in the various banks makes it possible to study the rate of evolution as a function of the mutational load.

5) The invention may be used to determine the optimal mutational load in mutated gene of interest banks to generate a batch of parental genes prior to the use of molecular recombination methods. The investigator firstly produces gene of interest banks with varying levels of mutation and then determines, by means of the method according to the invention, the mutational loads associated with the various banks. Secondly, performing suitable screening on the mutated gene of interest banks makes it possible to identify the clones displaying one or more enhanced properties with respect to those displayed by the wild protein. In this way, each of the mutated gene of interest banks generates a batch of optimised genes, used as parental genes in a recombination step. The various recombined gene banks are screened to identify even more enhanced proteins than those produced by the parental genes or by the wild protein. The analysis and comparison of these banks, for example on the frequency of occurrence of enhanced clones or on the quantification of the enhancements obtained. All in vitro recombination methods: DNA Shuffling (Stemmer W. (1994) Nature 370:389-391), L-Shuffling (WO0009679), StEP (Zhao H. et al. (1998) Nature Biotechnology 16:258-261), RACHiTT (Coco W. et al. (2001) Nature Biotechnology 19:354-359), and in vivo recombination methods such as recombination in yeast (Pompon D. et al. (1989) Gene 83:15-24), and in vivo chimerisation/repairs (Volkov A. et al. (1999) Nucleic Acids Research 27:e18) are concerned by the invention.

6) The method according to the invention may be used to quantify or compare the precision of one or more nucleic acid polymerisation methods. The investigator produces one or more model gene banks from the products obtained from polymerisation(s) carried out under given experimental conditions, buffer composition, polymerase type, etc.

Secondly, he/she determines, by means of the method according to the invention, the mutational loads associated with the model gene banks. The latter, after the incorporation if required of the number of replication cycles, make it possible to estimate the precision of the polymerisation method, under the experimental conditions used.

The present invention also relates to kits for the implementation of the method and its various applications or uses.

Such a kit comprises:
  at least one model gene for example in plasmid form;
  at least one chart used to associate the mutational load of a gene bank obtained by means of random mutagenesis with the fraction of mutated model genes observed in said bank;
  the reagents required for the implementation of the random mutagenesis technique such as a thermostable DNA polymerase, dNTP, magnesium, manganese, PCR buffer if the mutagenesis technique corresponds to error-prone PCR;
  the reagents, if required, to observe mutant model genes;
  instructions indicating the correction sub-factors defined for a parameter selected as influencing the mutational load.

There are the same number of charts as model genes in said kit.

In one embodiment wherein the mutagenesis technique uses an amplification step, the kit may comprise primers for the amplification of the model gene.

If the kit is used to obtain and control a desired mutational load in a mutated gene bank, it also contains at least one chart enabling it to associate the mutational load (ML) of a gene bank obtained by means of random mutagenesis of a model gene with the experimental random mutagenesis conditions.

The correction sub-factors provided will be completed by one or more of the following data, in a non-limitative manner, such as:
  the length of the gene of interest,
  the base A composition of the gene of interest,
  the base C composition of the gene of interest,
  the base G composition of the gene of interest,
  the base T composition of the gene of interest,
  the multiplication number of the model gene matrix
  the multiplication number of the gene of interest matrix,
  wherein the corresponding values are incorporated by the investigator according to the gene of interest. These data will be selected depending on whether it is desired to account for one or more intrinsic and/or experimental parameters.

If the model gene corresponds to gfp and the mutagenesis technique corresponds to error-prone PCR, the various correction sub-factors are those described above.

In one preferred embodiment, the kit contains several model genes and several charts for each model gene that has the most similar intrinsic properties to the gene of interest.

According to one particular embodiment of the use of the kit according to the invention, the correction sub-factors are recorded in a digital file saved on a suitable medium (CD-Rom, floppy disk, etc.).

Similarly, in a kit according to the invention, the chart may be recorded in the form of a digital database saved on a suitable medium.

Finally, the invention relates to a method wherein at least one of steps (a), (c) and (d) is implemented by data processing means.

Said data processing means may:
  be associated the mutational load of gene bank obtained by means of random mutagenesis of a model gene with the fraction of mutated model genes observed in said bank.
  be incremented by each new chart created. This method includes the use of a database of various charts, each being defined for a given mutagenesis technique and a model gene.
  comprise data to define at least one correction factor for the determination of the mutational load of a mutated gene of interest bank.

The investigator should then specify, according to his/her research, numeric data relating to at least one of the following characteristics processed by said data processing means:
  the model gene and its intrinsic properties
  the mutagenesis technique
  the parameter(s) selected as capable of influencing the mutational load of a gene bank with respect to another to define the correction sub-factors.

Said data processing means may be presented in the form of software.

Said software may be used on any type of multimedia device, such as for example, a pre-programmed calculator, or a PC, and comprises a simple interface enabling the investigator to specify the different numeric data using said data processing means.

Said software also makes it possible integrate the data associated with the charts of the model gene(s), and the correction sub-factors.

Said charts and correction sub-factors may be either recorded directly by the investigator in said software, or be recorded in a digital file saved on a suitable medium (CD-Rom, floppy disk, etc.), said medium being introduced into the multimedia device (PC, calculator, etc.) by the investigator at the required time.

For example, the investigator will enter one or more of the data already described above.

In this way, the invention also relates to:
  firstly, a multimedia device such as pre-programmed calculator or a PC for the implementation of the above method, and
  secondly, a device liable to be used in a method to determine the mutational load of a bank obtained following the random mutagenesis of a gene of interest comprising a kit defined above and said multimedia device.

Other advantages and characteristics of the invention will emerge in the following examples, wherein reference will be made to the appended figures wherein:

FIG. 1 represents the GFP gene sequence (SEQ ID NO:1).

FIG. 4 represents the target mutation matrix $M_{target}[gfp]$ on the gfp gene for the error-prone PCR random mutagenesis technique.

EXAMPLE 1

Figure 2:
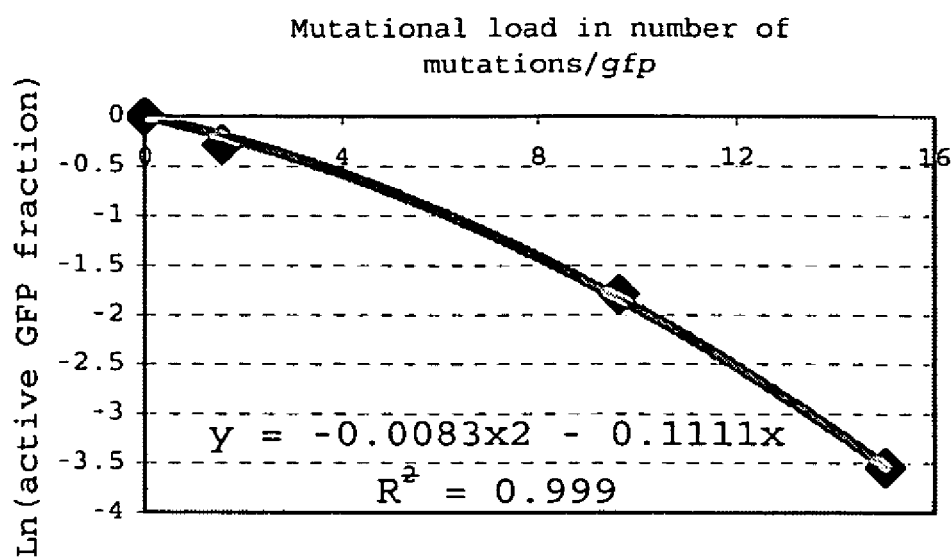
FIG. 2 represents the relationship between the clone fraction expressing a functional GFP and the mutational load in the mutated gfp gene bank.

Determination of the Mutational Load Introduced into a *Thermotoga maritima* (xynA) Xylanase Gene Bank Following a Random Mutagenesis Step Using the Following Steps 1) Model Gene Selection In the example developed, Green Fluorescent Protein gene (gfp) was selected as the model gene due to the easy implementation of a phenotypic test based on the expression of the gfp gene product: the colonies expressing a protein corresponding to "Green Fluorescent Protein" or functional GFP display a green colour in ultraviolet.

2) Random Mutagenesis Method Selection

Due to the their ease of use, the random mutagenesis was conducted by means of error-prone PCR as described by Cadwell (Cadwell R. C., Joyce G. F. (1992) PCR Methods Appl. 2:28-33).

3) Obtaining a Chart Used to Associate the Mutational Load of a Randomly Mutated gfp Model Gene Bank with the Fraction of Mutated Model Genes Observed in Said Bank To determine the correspondence between the mutational load in the mutated gfp model gene bank and the clone fraction expressing a functional GFP, three random mutagenesis experiments (A, B and C) were performed by means of error-prone PCR.

The error-prone PCR reactions were carried out in 100 µl volumes containing 10 mM of pH9 Tris-HCl, 50 mM of KCl, 0.1% Triton X-100, 0.2 mg/ml of BSA, 20 pmol of pET5' and pET3' universal primers, 2.5 U of Taq polymerase (QBiogen). The divalent cation concentrations are 4 mM $MgCl_2$ for experiment A, 7 mM $MgCl_2$ plus 0.3 mM $MnCl_2$ for experiment B and 7 mM of $MgCl_2$ plus 0.5 mM $MnCl_2$ for experiment C. The dNTP concentrations used are 0.2 mM of DATP, 0.2 mM of dGTP, 1 mM of dTTP and 1 mM of dCTP while 1 fmol of vector was used as the DNA matrix. A PCR programme of 94° C. for 5 min; (91° C. for 30 s, 60° C. for 30 s, 72° C. for 1 min.) 25 times followed by 72° C. for 10 min as a final elongation step, was applied in an MJ Research PTC-200 thermocycler.

The PCR products were purified using the purification kit on a QIAquick column (Qiagen), verified on gel and the quantities of DNA obtained were quantified using the PicoGreen kit (Molecular Probes) as described by the supplier.

The error-prone PCR products (1 µg) were digested by Eco RI and Nde I (New England Biolabs) for 1 hour at 37° C. in the suitable reaction buffer as described by the supplier and purified on a QIAquick column and inserted into the pET26b+ vector (Stratagene) previously digested with Eco RI and Nde I. The *E. coli* MC1061(DE3) cells were transformed by means of a thermal shock as described by Maniatis (Sambrook J. et al. (1989) Molecular cloning: a laboratory manual Cold Spring Harbor Laboratory Press—New York) with 1 µl of the ligation reactions. The transformants were selected on LB agar dishes supplemented with 0.6 mg/ml of kanamicin.

After cloning and transformation, the three banks are analysed for the clone fraction expressing a functional GFP but also by sequencing to determine the mutational loads in the three mutated gfp gene banks following mutagenesis experiments A, B and C.

The screening of the clones expressing a functional GFP protein was performed by identifying the colonies displaying green fluorescence under a UV bench (excitation wavelength at 355 nm). In parallel, the mutated gfp gene insertion yield in the various banks was analysed by means of PCR on colonies selected at random. For each bank, the screening to detect clones displaying a functional GFP was performed on approximately 1000 clones and the insertion yield (number of clones displaying one insert per total number of clones) was estimated on the basis of 96 PCR on colonies, so as to be statistically relevant.

The mutated gfp gene banks are thus analysed on the total number of colonies (cfu_total), the number of colonies expressing a functional GFP (cfu_fluo) and the mutated gfp gene insertion yield in the banks (Ri). The clone fraction expressing a functional GFP in a given bank (Fa[GFP]) is then deduced as follows:

$$Fa[GFP] = \frac{cfu\_fluo}{cfu\_total \times Ri}$$

TO determine the mutational loads in mutated gene banks A, B or C, 24 clones per bank containing a gfp insert were selected for PCR amplification with the primers pET5'/pET3'. The digestion products were purified on a QIAquick column and then sequenced in their entirety. All the mutations (base modification, insertion and deletion) detected in the sequences with respect to that displayed by the wild gfp gene were verified on chromatograms.

For each of the three banks, the sequencing was conducted on 13623 to 15774 pb. The sequencing of a sufficiently large number of bases makes it possible to obtain a statistically reliable measurement of the mutational loads, even in the case of the bank containing the least mutated genes (bank A). It should be noted that the ratio between the clones expressing a functional GFP and those expressing an inactive GFP was retained for the selection of the 24 clones dedicated for sequencing. In fact, it has been described that, following a random mutagenesis step, the genes coding for an active protein could have a lower mutational load than non-selected genes (Daugherty P et al. (2000) Proc. Natl. Acad. Sci. USA. 97:2029-2034). In this way, random selection for the sequencing of a statistically low number of clones could have biased the observation of the mutational load.

Table 2 below represents the analysis of the clone fraction expressing a functional GFP as a function of the mutational load of the mutated gfp banks. It summarises the results obtained on the analysis of the GFP phenotypic test, while FIG. 2 shows the logarithm of the functional GFP fraction as a function of the mutational load in the mutated gfp banks.

TABLE 2

| Experiment PCR-ep | Reaction conditions | | Number of pb sequenced | Number of mutations | Mutational load (mutations/gfp) | Functional GFP fraction (%) |
| --- | --- | --- | --- | --- | --- | --- |
| | [MgCl2] mM | [MnCl2] | | | | |
| A | 4 | 0 | 15057 | 33 | 1.57 | 75.1 |
| B | 7 | 0.3 | 15774 | 212 | 9.64 | 16.5 |
| C | 7 | 0.5 | 13623 | 285 | 15 | 2.9 |

On the basis of the data generated, it is possible to define an order 2 polynomial regression curve, representing the chart according to the following equation:

$$\ln(Fa[GFP])=-0.0083 \times ML[gfp]^2-0.1111 \times ML[gfp]$$

associating the mutational load of a gene bank obtained by means of error-prone PCR of the gfp model gene (M.L.[gfp]) with the fraction of mutated gfp genes observed in said bank during the phenotypic test (Fa[GFP]).

As the value of the coefficient of regression ($R^2$) is 0.999 (see FIG. 2), the chart determined above makes it possible to estimate precisely the mutational load in a mutated gfp gene bank following a random mutagenesis step by means of error-prone PCR using the clone fraction expressing a functional GFP.

Figure 3:
FIG. 3 represents the mutation matrix $Mut_{GFP}$ for the gfp model gene and for the error-prone PCR random mutagenesis technique.

The analysis of the sequencings on mutated gfp genes also made it possible to analyse the mutation matrix $Mut_{GFP}$ (FIG. 3) and deduce the target mutation matrix on the gfp gene, $M_{target}[gfp]$ (FIG. 4).

4) Application in Parallel of Random Mutagenesis to the gfp Model Gene and the *Thermotoga maritima* xynA Gene of Interest The xynA xylanase gene obtained from *Thermotoga maritima* (accession number EMBL Z46264) was subjected to random mutagenesis by means of error-prone PCR with 7 mM $MgCl_2$ and 0.3 mM $MnCl_2$ (conditions B). The experimental protocol is identical to that described above, except that the PCR elongation step was set to 3 minutes instead of 1 min. It should be noted that the same reaction mixture was used for the error-prone PCR on the gfp gene and for the error-prone PCR on the xynA gene. The use of the gfp gene as an internal standard within the scope of the invention should make it possible to eliminate experimental variations on mutational loads in mutated gfp model gene banks.

The yields of the error-prone PCR experiments were determined by comparison with a known quantity of DNA standard after migration of 1 µl of reaction on 1% agarose gel. As the initial quantity of vector was 1 fmole in each of the two experiments conducted, the multiplication number (d) was determined at 15 and 12 for the gfp and xynA error-prone PCRs, respectively.

5) Determination of Mutational Load of Bank Obtained from gfp Model Gene

Following the error-prone PCR conducted under conditions B, the fraction of gfp genes coding for a functional protein in the bank was determined at 0.165.

Using the chart given by the following equation (equation 4):

$$\ln(Fa[GFP])=-0.0083 \times ML[gfp]^2-0.1111 \times ML[gfp]$$

associating the mutational load of a mutated gfp model gene bank with the fraction of mutated model genes observed, the mutational load in the mutated gfp bank is simulated at 9.5 mutations per gene.

It should be noted that the mutational load in said bank was determined by sequencing at 9.64 mutations per gene i.e. a 1.5% error between the mutational load given by the chart and that given by sequencing.

6) Determination of the Mutational Load Introduced into the Mutated xynA Gene Bank Obtained by Means of the Mutational Load in the Mutated gfp Model Gene Bank The mutational load introduced into the mutated xynA gene bank following the error-prone PCR experiment is determined by correcting the mutational load calculated in the mutated gfp gene bank with the correction factor C.F. defined according to the following equation:

$$M.L.(\text{gene of interest})=M.L.(\text{model gene}) \times C.F.$$

wherein, C.F. represents the correction factor and M.L. represents the mutational load.

a) Accounting for at Least One Intrinsic Parameter

In this analysis, the intrinsic parameter selected in the gene length, which is recognised by those skilled in the art as having a significant influence on the mutational load of mutated gene banks.

The model gene corresponding to gfp and the mutagenesis technique corresponding to error-prone PCR, the single correction sub-factor corresponds such that:

intrinsic parameter 1=gene length

Where C.F.[L]=L(gene of interest)/717 where L is expressed in number of base pairs.

Table 3 below reproduces the main intrinsic parameters, particularly the length of the gfp model gene and the xynA gene of interest.

TABLE 3

| Gene | L (pb) | Base composition (%) | | | |
|---|---|---|---|---|---|
| | | A | T | C | G |
| gfp | 717 | 34 | 26 | 19.7 | 20.3 |
| xynA | 3120 | 32 | 19 | 23 | 26 |

In this way, the resolution gives:

$$C.F.=C.F.[L]=3120/717=4.35$$

Following the simulation with the length as the only intrinsic parameter, the mutational load calculated in the xynA gene bank is:

$$M.L.[xynA]sim1=4.35 \times 9.5=41.3 \text{ mutations}/xynA \text{ gene}$$

b) Accounting for at Least Two Intrinsic Parameters and One Experimental Parameter In this analysis, more detailed than the previous analysis, the selected intrinsic parameters are the gene length and the base composition. The experimental parameter selected is the DNA matrix multiplication number for error-prone PCR. These parameters are known to those skilled in the art as being able to influence the mutational load in gene banks following mutagenesis by means of error-prone PCR.

The model gene corresponding to gfp and the mutagenesis technique corresponding to error-prone PCR, different correction sub-factors correspond such that:

intrinsic parameter 1 represents the length of the genes according to the following equation:

$$C.F.[L]=L(\text{gene of interest})/717$$

where L is expressed in number of base pairs.

intrinsic parameter 2 represents the base composition on the DNA strands according to the following equation:

$$\text{Where } C.F.\ [\text{base}] = \left( \frac{0.506 \times A(g \cdot \text{interest})}{0.34} + \frac{0.063 \times T(g \cdot \text{interest})}{0.26} + \frac{0.063 \times C(g \cdot \text{interest})}{0.197} + \frac{0.085 \times G(g \cdot \text{interest})}{0.203} \right)$$

where $A_{(g.interest)}$, $T_{(g.interest)}$, $C_{(g.interest)}$ and $G_{(g.interest)}$ are in fractions.

experimental parameter represents the multiplication rate according to the following equation:

$$C.F.[d]=d(\text{gene of interest})/d(gfp)$$

Table 3 contains the main intrinsic parameters, length and base composition, of the gfp model gene and the xynA gene of interest. Moreover, following the error-prone PCRs conducted on the gfp model gene and the xynA gene of interest, the multiplication rates are 15 and 12 for gfp and xynA respectively.

The resolution gives:

$C.F.[L]=3120/717=4.35$ $C.F.[d]=12/15=0.80$ $$C.F.\ [base] = \left(\frac{0.506\times 0.32}{0.34} + \frac{0.346\times 0.19}{0.26} + \frac{0.063\times 0.23}{0.197} + \frac{0.085\times 0.26}{0.203}\right) = 0.91$$

As the correction factor C.F. is constructed by multiplying the various sub-factors taken into account for the determination of the mutational load of the mutated gene of interest bank:

$C.F.=C.F.[L]\times C.F.[base]\times C.F.[d]$ i.e.:

$C.F.=4.35\times 0.91\times 0.8=3.17$

Following the simulation with the length and the base composition as intrinsic parameters and the multiplication rate as the experimental parameter, the mutational load calculated in the mutated xynA gene bank is:

$M.L.[xynA]sim2=3.17\times 9.5=30.1$ mutations/$xynA$ gene

The mutational load in the mutated xynA gene bank was also determined by means of sequencing to validate the mutational load determination methods according to the invention.

Two mutated recombinant *Thermotoga* maritime xynA genes were selected for sequencing. The mutated xylanase genes were entirely sequenced as described in example 1, (3).

Of the 38160 pb sequenced, 381 mutations were detected in the mutated xynA genes. In this way, the mutational load observed in the mutated xynA gene bank is 31.8 mutations/xynA gene.

The error recorded between the mutational load observed and the simulated mutational load in the xynA gene bank is 29.9% for simulation 1 (performed with only the length as an intrinsic parameter), and 5.3% for simulation 2 (performed with the length and base composition as intrinsic parameters and the multiplication rate as the experimental parameter).

The inclusion, in the simulations, of the base composition and the multiplication rate of the gfp model gene and the xynA gene of interest makes it possible to reduce the error on the mutational load by approximately a factor of six. Such a result underlines the interest of incorporating in the correction factor C.F. not only the gene length but also the greatest number of intrinsic and experimental parameters identified as being liable to influence the mutational load.

In addition, the accuracy of the mutational load result obtained within the scope of simulation 2 with respect to that observed during sequencing (less than 6% error) demonstrates the relevance of the invention as a possible reliable replacement of the mutational load study in a mutated gene bank by means of sequencing.

All the results on the mutational loads simulated or observed in the mutated xynA gene bank are shown in table 4 below.

This table 4 summarises the mutational load results on a mutated xynA gene bank, observed by means of sequencing (M.L.[xynA]obs), simulated by accounting only for the gene length (simulation A) or simulated by accounting for the gene length, base composition and the DNA matrix multiplication number (simulation B).

TABLE 4

| Simulation | M.L. [xynA]sim | Error sim./obs. |
|---|---|---|
| A | 41.3 | 29.9% |
| B | 30.1 | 5.3% |
| M.L. [xynA]obs | 31.8 | |

EXAMPLE 2

Analysis of Protein Plasticity of TEM-1 β-Lactamase

This analysis is performed according to the following steps:
1) model gene selection;
2) random mutagenesis method selection;
3) obtaining a chart used to associate the mutational load of a randomly mutated gfp model gene bank with the fraction of mutated model genes observed in said bank;

These steps are identical to those developed in example 1. However, this example comprises the steps 4 to 7 described below.

4) Application in Parallel of Random Mutagenesis by Means of Error-Prone PCR to the gfp Model Gene and the TEM-1 Gene of Interest The gfp model gene and the TEM-1 gene of interest (accession number EMBL AAR25033) were subjected to four random mutagenesis experiments by means of error-prone PCR with 4 mM $MgCl_2$ (condition I), 7 mM $MgCl_2$ plus 0.15 mM $MnCl_2$ (condition II), 7 mM $MgCl_2$ plus 0.3 mM $MnCl_2$ (condition III) and 7 mM $MgCl_2$ plus 0.5 mM $MnCl_2$ (condition IV). The experimental protocol is identical to that described in example 1.

The yields of the error-prone PCR experiments were determined as described in example 1. The multiplication rate was thus determined at 15 and 14 for the gfp and TEM-1 error-prone PCRs respectively.

5) Determination of Mutational Loads in Banks Obtained from gfp Model Gene

Following the four error-prone PCR experiments, the fractions of the mutated gfp gene banks coding for a functional GFP protein were determined with the following equation (equation 3):

$$Fa[GFP] = \frac{cfu\_fluo}{cfu\_total\times Ri}$$

The determination of the mutational loads in the mutated gene banks is performed using the chart described in the following equation (equation 4):

$\ln(Fa[GFP])=-0.0083\times ML[gfp]^2-0.1111\times ML[gfp]$ on the basis of the gfp gene fraction coding for an active GFP protein (Fa[GFP]).

Table 5 below contains the results obtained following this analysis. It gives the mutational loads in the mutated gfp gene banks on the basis of the phenotypic test analysis implemented on the GFP protein. Ri is the mutated gfp gene insertion yield in the various banks, determined by means of PCR/colony; cfu_total and cfu_fluo are the number of clones analysed and the number of fluorescent green clones in U.V. respectively; Fa[GFP] is the functional GFP clone fraction while M.L.[gfp] is the mutational load in the various mutated gfp gene banks.

TABLE 5

| PCR-ep conditions | cfu_total | cfu_fluo | Ri | Fa[GFP] | M.L. [gfp] |
|---|---|---|---|---|---|
| I | 270 | 226 | 0.958 | 0.874 | 1.1 |
| II | 240 | 179 | 0.958 | 0.550 | 4.1 |
| III | 775 | 135 | 0.958 | 0.182 | 9.1 |
| IV | 1160 | 52 | 0.958 | 0.047 | 13.6 |

6) Determination of the Mutational Loads Introduced into the Mutated TEM-1 Gene Banks Obtained by Means of the Mutational Loads in the Mutated gfp Model Gene Banks As above, the mutational loads introduced into the mutated TEM-1 gene bank following the error-prone PCR experiments are determined by correcting the mutational loads calculated in the mutated gfp model gene banks with the correction factor C.F. defined according to the following equation (equation 1):

$$M.L.(\text{gene of interest}) = M.L.(\text{model gene}) \times C.F.$$

where C.F. represents the correction factor and M.L. represents the mutational load.

To obtain maximum precision on the determination of the mutational loads in the mutated TEM-1 gene banks, the correction factor is calculated by accounting for two intrinsic parameters (gene length and base composition) and one experimental parameter (DNA matrix multiplication rate during error-prone PCR).

The model gene corresponding to gfp and the mutagenesis technique corresponding to error-prone PCR, different correction sub-factors correspond such that:

intrinsic parameter 1 represents the length of the genes according to the following equation:

$$C.F.[L] = L(\text{gene of interest})/717$$

where L is expressed in number of base pairs.

intrinsic parameter 2 represents the base composition on the DNA strands according to the following equation:

$$\text{Where } C.F.\ [\text{base}] = \left( \frac{0.506 \times A(g \cdot \text{interest})}{0.34} + \frac{0.346 \times T(g \cdot \text{interest})}{0.26} + \frac{0.063 \times C(g \cdot \text{interest})}{0.197} + \frac{0.085 \times G(g \cdot \text{interest})}{0.203} \right)$$

where $A_{(g.interest)}$, $T_{(g.interest)}$, $C_{(g.interest)}$ and $G_{(g.interest)}$ are in fractions.

experimental parameter represents the multiplication rate according to the following equation:

$$C.F.[d] = d(\text{gene of interest})/d(gfp)$$

Table 6 contains the main intrinsic parameters, length and base composition, of the gfp model gene and the TEM-1 gene of interest. Moreover, following the error-prone PCRs conducted on the gfp model gene and the xynA gene of interest, the multiplication rates are 15 and 14 for gfp and TEM-1 respectively.

TABLE 6

Intrinsic parameters of gfp model gene and TEM-1 gene of interest.

| Gene | L (pb) | Base composition (%) | | | |
|---|---|---|---|---|---|
| | | A | T | C | G |
| gfp | 717 | 34 | 26 | 19.7 | 20.3 |
| TEM-1 | 861 | 25.9 | 24.7 | 23.6 | 25.8 |

The resolution gives:

$$C.F.[L] = 861/717 = 1.2$$

$$C.F.\ [\text{base}] = \left( \frac{0.506 \times 0.259}{0.34} + \frac{0.346 \times 0.247}{0.26} + \frac{0.063 \times 0.236}{0.197} + \frac{0.085 \times 0.258}{0.203} \right) = 0.9$$

$$C.F.[d] = 14/15 = 0.93$$

i.e.:

$$C.F. = 1.2 \times 0.9 \times 0.93 = 1.01$$

In the determination of the correction factor C.F., the greater length of the TEM-1 gene is compensated for by a higher percentage of base C and G and a decrease in the error-prone PCR yield in the case of the TEM-1 gene with respect to the gfp model gene.

Following the simulation with two intrinsic parameters and one experimental parameter, the mutational loads calculated in the TEM-1 gene banks are:

For condition I:

$$M.L.[TEM\text{-}1]sim = 1.01 \times 1.1 = 1.1 \text{ mutations}/TEM\text{-}1 \text{ gene}$$

For condition II:

$$M.L.[TEM\text{-}1]sim = 1.01 \times 4.1 = 4.1 \text{ mutations}/TEM\text{-}1 \text{ gene}$$

For condition III:

$$M.L.[TEM\text{-}1]sim = 1.01 \times 9.1 = 9.2 \text{ mutations}/TEM\text{-}1 \text{ gene}$$

For condition IV:

$$M.L.[TEM\text{-}1]sim = 1.01 \times 13.6 = 13.7 \text{ mutations}/TEM\text{-}1 \text{ gene}$$

6) Analysis of Protein Plasticity of TEM-1 β-Lactamase

The protein plasticity study requires being able to associate the survival rate of the products of the mutated gene of interest, under a given screen, in a mutated gene of interest bank as a function of the mutational load in said bank (Shafikhani S. et al. (1997) BioTechniques 23:304-310/Daugherty P. et al. (2000) Proc. Natl. Acad. Sci. USA 97:2029-2034).

To analyse the survival rate of TEM-1 β-lactamase in the four error-prone PCR banks generated above, the PCR products (1 µg) were digested by Eco RI and Nde I (New England Biolabs) for 1 hour at 37° C. in the suitable reaction buffer as described by the supplier and purified on a QIAquick column and inserted into the pET26b+vector (Stratagene) previously digested with Eco RI and Nde I. The *E. coli* MC1061(DE3) cells were transformed by means of a thermal shock as described by Maniatis (Sambrook J. et al. (1989) Molecular cloning: a laboratory manual Cold Spring Harbor Laboratory Press—New York) with 5 µL of the ligation reactions. The number of transformants in the various banks was estimated by spreading a fraction of the bank on LB agar dishes supplemented with 0.6 mg/ml of kanamicin while the number of clones expressing a functional TEM-1 β-lactamase was estimated by spreading the remainder of the bank on LG agar dishes supplemented with 0.6 mg/ml of kanamicin and 10 µg/ml of ampicillin. The mutated TEM-1 gene insertion yield was estimated by means of PCR on colonies as described above.

Table 7 contains the results obtained on the survival rates of mutated TEM-1 β-lactamase proteins in the four error-prone banks. The functional TEM-1 clone fraction (Fa[TEM]) is determined on the basis of the mutated TEM-1 gene insertion yield (Ri), the number of clones analysed (cfu_total) and the number of ampicillin-resistant clones (cfu_R).

TABLE 7

Survival rate of TEM-1 β-lactamase protein in the four error-prone PCR banks.

| Conditions | cfu_total | cfu_R | Ri | Fa[TEM] |
|---|---|---|---|---|
| I | 761 | 539 | 0.958 | 0.739 |
| II | 746 | 265 | 0.958 | 0.371 |
| III | 1215 | 55 | 0.938 | 0.048 |
| IV | 1143 | 7 | 0.938 | 0.0065 |

Figure 5:
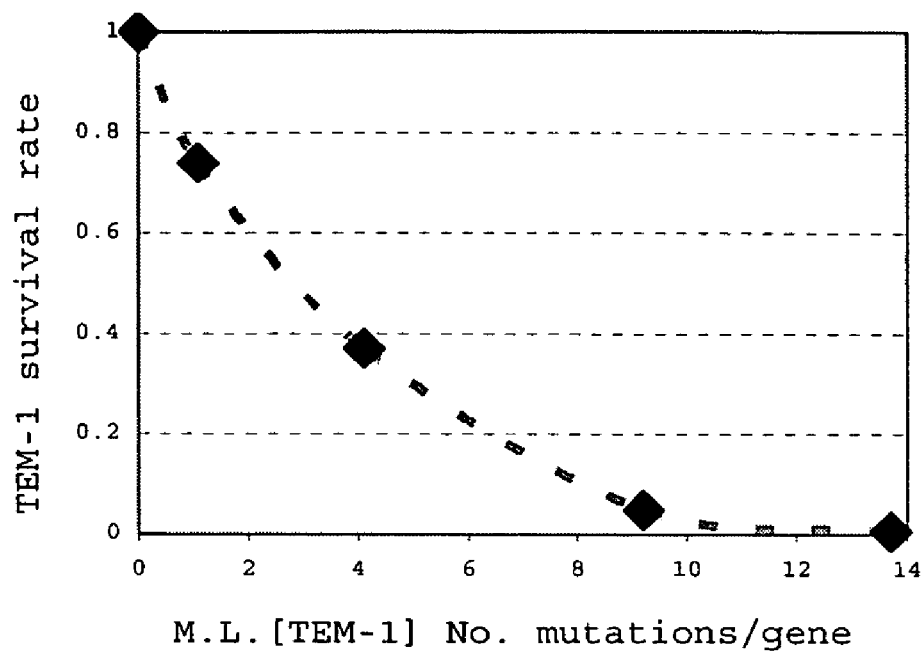
FIG. 5 represents the plasticity of TEM-1 β-lactamase, i.e. the survival rate of mutated proteins as a function of the mutational load of mutated TEM-1 gene banks.

FIG. 5 shows the protein plasticity analysis of TEM-1 Beta-lactamase, i.e. the survival rate of mutated TEM-1 Beta-lactamase proteins as a function of the mutational load in mutated TEM-1 gene banks.

In conclusion, the present invention makes it possible to study, in a particular embodiment, the protein plasticity without using sequencing.

EXAMPLE 3

Analysis of Evolution of TEM-1 Beta-Lactamase Towards Cefotaxim Antibiotic Resistance as a Function of the Mutational Load of the Error-Prone PCR Banks This analysis comprises the following steps:

1) model gene selection.

2) random mutagenesis method selection.

3) obtaining a chart used to associate the mutational load of a randomly mutated gfp model gene bank with the fraction of mutated model genes observed in said bank.

These steps are identical to those developed in examples 1 and 2. However, this analysis also comprises steps 4-7 described below.

4) Application in Parallel of Random Mutagenesis by Means of Error-Prone PCR to the gfp Model Gene and the TEM-1 Gene of Interest The gfp model gene and the TEM-1 gene of interest were subjected to five random mutagenesis experiments by means of error-prone PCR with 5 mM $MgCl_2$ (condition 1), 7 mM $MgCl_2$ plus 0.1 mM $MnCl_2$ (condition 2), 7 mM $MgCl_2$ plus 0.2 mM $MnCl_2$ (condition 3), 7 mM $MgCl_2$ plus 0.3 mM $MnCl_2$ (condition 4) and 7 mM $MgCl_2$ plus 0.5 mM $MnCl_2$ (condition 5). The experimental protocol is identical to that described in example 2.

The yields of the error-prone PCR experiments were determined as described in example 1 and are identical to those found in example 2. The multiplication rate is 15 and 14 for the gfp and TEM-1 error-prone PCRs respectively.

5) Determination of Mutational Loads in Banks Obtained from gfp Model Gene

Following the five error-prone PCR experiments, the fractions of the mutated gfp gene banks coding for a functional GFP protein were determined with the following equation (equation 3):

$$Fa[GFP] = \frac{cfu\_fluo}{cfu\_total \times Ri}$$

The determination of the mutational loads in the mutated gene banks is performed using the chart described in the following equation:

$$\ln(Fa[GFP]) = -0.0083 \times ML[gfp]^2 - 0.1111 \times ML[gfp]$$

on the basis of the gfp gene fraction coding for an active GFP protein (Fa[GFP]).

Table 8 below contains the results obtained following this analysis. This table reports the determination of the mutational loads in the mutated gfp gene banks on the basis of the analysis of the GFP phenotypic test. Ri is the mutated gfp gene insertion yield in the various banks, cfu_total and cfu_fluo are the number of clones analysed and the number of fluorescent green clones in U.V., Fa[GFP] is the functional GFP clone fraction while M.L. [gfp] is the mutational load in the various mutated gfp gene banks.

TABLE 8

| PCR-ep conditions | cfu_total | cfu_fluo | Ri | Fa[GFP] | M.L. [gfp] |
|---|---|---|---|---|---|
| 1 | 425 | 305 | 0.96 | 0.749 | 2.2 |
| 2 | 450 | 268 | 0.96 | 0.621 | 3.4 |
| 3 | 568 | 212 | 0.96 | 0.389 | 5.9 |
| 4 | 842 | 100 | 0.96 | 0.124 | 10.5 |
| 5 | 1093 | 26 | 0.75 | 0.034 | 14.8 |

6) Determination of the Mutational Loads Introduced into the Mutated TEM-1 Gene Banks Obtained by Means of the Mutational Loads in the Mutated gfp Model Gene Banks The correction factor is calculated by accounting for two intrinsic parameters, the gene length and base composition and one experimental parameter, the DNA multiplication rate during error-prone PCR.

As the gfp model gene and the TEM-1 gene of interest are identical to those in example 2 and the multiplication rates are also unchanged between examples 1 and 2, the correction factor C.F. is identical to that determined in example 2.

I.e. C.F.=1.01

Following the simulation with two intrinsic parameters and one experimental parameter, the mutational loads calculated in the five mutated TEM-1 gene banks are:

For condition 1:

$M.L.[TEM\text{-}1]sim = 1.01 \times 2.2 = 2.2$ mutations/$TEM\text{-}1$ gene

For condition 2:

$M.L.[TEM\text{-}1]sim = 1.01 \times 3.4 = 3.4$ mutations/$TEM\text{-}1$ gene

For condition 3:

$M.L.[TEM\text{-}1]sim = 1.01 \times 5.9 = 6.0$ mutations/$TEM\text{-}1$ gene

For condition 4:

$M.L.[TEM\text{-}1]sim = 1.01 \times 10.5 = 10.6$ mutations/$TEM\text{-}1$ gene

For condition 5:

$$M.L.[TEM\text{-}1]sim = 1.01 \times 14.8 = 14.9 \text{ mutations}/TEM\text{-}1 \text{ gene}$$

7) Analysis of Cefotaxim Resistance Acquisition of Mutated Recombinant TEM-1 β-Lactamase Clones The selected evolution system describes the influence of the mutational load of the mutated TEM-1 gene bank on the frequency of occurrence of cefotaxim-resistant clones due to evolution of the TEM-1 gene.

To analyse the frequency of occurrence of resistant clones, the PCR products are cloned in pET26b+vector as described above to form 5 mutated TEM-1 gene banks. The clone banks are produced by means of electrotransformation of E. coli MC1061(DE3) cells with 10×2 μl of ligation. The number of transformants in each of the five banks was estimated by spreading $\frac{1}{25}^{th}$ of the bank on LB agar dishes supplemented with 0.6 mg/ml of kanamicin while the cefotaxim-resistant clones were isolated by spreading the remainder of the bank ($\frac{24}{25}^{ths}$) on LB agar dishes supplemented with 0.6 mg/ml of kanamicin and 15 ng/ml of cefotaxim. The mutated TEM-1 gene insertion yield was estimated by means of PCR on colonies.

Table 9 below contains the results obtained on the frequency of occurrence of clones, resistant to cefotaxim, in the 5 mutated TEM banks. The frequency of enhanced clones in the various banks is calculated on the basis of the number of cefotaxim-resistant clones (cfu_cefoR) and the number of recombinant clones (Nb_recomb.), in turn deduced from the number of clones in the bank (cfu_total) and the mutated TEM-1 gene insertion yield (Ri).

TABLE 9

| Conditions | cfu_total | Ri | Nb_recomb | cfu_cefoR | Enhanced freq. ‰ |
|---|---|---|---|---|---|
| 1 | 103200 | 0.96 | 98900 | 51 | 0.516 |
| 2 | 53750 | 0.96 | 51510 | 41 | 0.796 |
| 3 | 189000 | 0.96 | 181125 | 50 | 0.276 |
| 4 | 158000 | 0.94 | 148125 | 18 | 0.122 |
| 5 | 223500 | 0.92 | 204875 | 11 | 0.054 |

Figure 6:
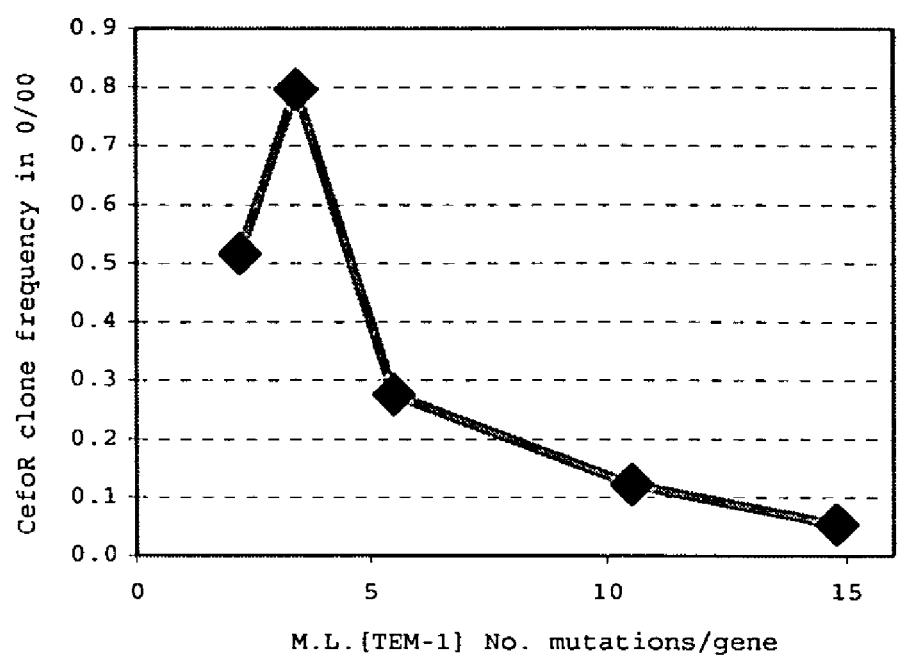
FIG. 6 represents the progression of TEM-1 β-lactamase, the frequency of occurrence of cefotaxim-resistant clones as a function of the mutational load of mutated TEM-1 gene banks.

FIG. 6 shows the influence of the mutational load of mutated TEM-1 gene banks on the frequency of occurrence of an enhanced TEM-1 variant.

The frequency of occurrence of cefotaxim-resistant clones as a function of the mutational load follows a bell-shaped curve passing via an optimal mutational load.

In this way, the method according to the invention may be used to analyse the evolution rate of mutated gene banks and also to obtain the optimal mutational load, without using sequencing.

In conclusion, this example also demonstrates the importance of controlling the mutational load precisely in mutated gene banks as the frequency of occurrence of cefotaxim-resistant TEM-1 variants is decreased by a factor of three for a mutational load passing from 3.4 to 6 mutations per TEM-1 gene. The present invention enables, without sequencing, a much finer control than the methods proposed by the prior art and meets this type of requirement perfectly.

EXAMPLE 4

Comparison and Estimation of the Precision of a Set of DNA Polymerase in a Given PCR Reaction This particular embodiment of the invention comprises the following steps:
1) model gene selection.
2) random mutagenesis method selection.
3) obtaining a chart used to associate the mutational load of a randomly mutated gfp model gene bank with the fraction of mutated model genes observed in said bank.

These steps are identical to those developed in examples 1 to 3. The analysis also comprises the steps 4-6 described below.

4) Application in Parallel of PCR to the gfp Model Gene with a Set of DNA Polymerase The gfp model gene was subjected to three PCR experiments containing 7 mM of MgCl$_2$ and 0.2 mM of MnCl$_2$. The experimental protocol is identical to that described in the above examples with an elongation time of 1 minute, except that 2.5 U of Taq polymerase (Q-Biogen), Vent$_R$ (New England Biolabs) or Pfu Turbo (Stratagène) were used as DNA polymerase.

The yields of the PCR experiments were determined as described above. The multiplication number is $d_A$, $d_B$ and $d_C$ for the PCRs performed with Taq DNA polymerase, Vent$_R$ DNA polymerase and Pfu DNA polymerase respectively.

5) Determination of Mutational Loads in Banks Obtained from gfp Model Gene

Following the PCR experiments, the fractions of the mutated gfp gene banks coding for a functional GFP protein were determined with the following equation (equation 3):

$$Fa[GFP] = \frac{cfu\_fluo}{cfu\_total \times Ri}$$

The mutational loads in the mutated gfp gene banks are determined using the chart described in the following equation (equation 4):

$$\ln(Fa[GFP]) = -0.0083 \times ML[gfp]^2 - 0.1111 \times ML[gfp]$$

on the basis of the gfp gene fraction coding for an active GFP protein (Fa[GFP]).

The mutational loads are A, B and C for the PCRs performed with Taq DNA polymerase, Vent$_R$ DNA polymerase and Pfu DNA polymerase respectively.

6) Comparison of Precision of the Three Polymerases used in the PCR Experiments

The error rates of the various polymerases in the reaction conditions used are deduced from the mutational loads in the mutated gfp gene banks by standardising by means of the gfp model gene length and the PCR multiplication rates.

The length of the gfp model gene is 717 base pairs and the multiplication rates following the PCRs are $d_A$, $d_B$ and $d_C$ with Taq DNA polymerase, Vent$_R$ DNA polymerase and Pfu DNA polymerase respectively.

In this way:

Error rate[Taq DNA polymerase]=$A/(717 \times d_A)$error/ pb/duplication

Error rate[Vent$_R$ DNA polymerase]=$B/(717 \times d_B)$error/ pb/duplication

Error rate[Pfu DNA polymerase]=$C/(717 \times d_C)$error/ pb/duplication

In conclusion, the method according to the invention makes it possible to determine accurately the precisions of a set of DNA polymerase in a given reaction mixture without using sequencing, while eliminating experimental condition variations.

The invention claimed is:

1. A method to determine the mutational load of a gene bank obtained by random mutagenesis of a gene of interest, comprising the following steps:
   a) obtaining a chart linking the mutational load (ML) of the gene bank obtained by random mutagenesis of a model gene with the fraction of mutated model genes observed in said bank;
   b) performing, in parallel, the random mutagenesis of the model gene used for the preparation of the chart for step (a) and the gene of interest to obtain the corresponding mutated gene banks;
   c) determining the mutational load (ML) of the gene bank obtained using the model gene in step (b) on the basis of the chart plotted in step (a);
   d) applying a correction factor (CF) to the mutational load (ML) of the mutated model gene bank determined in step (c) to determine the mutational load (ML) in the gene bank of the mutated gene of interest from step (b), wherein the correction factor (CF) comprises at least two intrinsic parameters of a characteristic of a gene and at least one experimental parameter.

2. The method according to claim 1, wherein the random mutagenesis used in step (b) is identical for the model gene, and for the gene of interest, and is also similar to that of step (a) in preparing the chart on the basis of the model gene in step (a).

3. The method according to claim 1, wherein steps (c) and (d) do not comprise sequencing.

4. The method according to claim 1, wherein the preparation of the chart in step (a), the observation of the mutated model genes in said bank is performed by analyzing one or more modifications of one or more properties of the nucleotide sequence of the mutated model genes directly or indirectly with respect to the model gene before mutagenesis.

5. The method according to claim 4, wherein said observation consists of observing the modification of one or more properties of the protein encoded by the model gene.

6. The method according to claim 5, wherein the observation of the modification of one or more properties of the protein encoded by the model gene is performed by means of a phenotypic test.

7. The method according to claim 1, wherein the model gene has characteristics shared by a large number of genes.

8. The method according to claim 1, wherein the model gene encodes a GFP protein.

9. The method according to claim 1, wherein the model gene has characteristics similar to those of the gene of interest.

10. The method according to claim 7 or 9, wherein the characteristics of the model gene comprise:
   its length,
   its base composition,
   its frequency of bases repeated in the sequence,
   the presence of symmetric sequences in the gene, or
   combinations thereof,
wherein the base composition corresponds to the percentage of base A, T, C, and G of one sequence strand of the model gene.

11. The method according to claim 1, wherein the random mutagenesis according to steps (a) and (b) uses polymerization.

12. The method according to claim 11, wherein the polymerization is error-prone PCR.

13. The method according to claim 1, wherein, in step (b), the same reaction mixture is used for the mutagenesis of the model gene and the gene of interest.

14. The method according to claim 1, wherein the intrinsic parameter of a characteristic of a gene is:
   its length,
   its base composition,
   bases represented in the sequence,
   the presence of symmetric sequences in the gene, or
   combinations thereof
wherein the base composition corresponds to the percentage of base A, T, C, and G of one sequence strand of the model gene.

15. The method according to claim 14, wherein the intrinsic parameters are gene length and base composition, wherein the base composition corresponds to the percentage of base A, T, C, and G of one sequence strand of the model gene.

16. The method according to claim 15, wherein the
   the experimental parameter is gene amplification rate during the mutagenesis step.

17. The method according to claim 1, wherein the experimental parameters, when mutagenesis is performed by chain amplification using a polymerase, is:
   the gene amplification rate during the mutagenesis step,
   the quantity of initial matrix,
   the number of amplification cycles,
   the type and quantity of polymerase used,
   the experimental conditions used such as the divalent cation concentration, the dNTP concentration and concentration ratio, or
   combinations thereof.

18. The method according to claim 1, wherein at least one intrinsic parameter and at least one experimental parameter are taken into consideration to determine the correction factor.

19. The method according to claim 1, wherein the mutagenesis is performed by means of error-prone PCR, the model gene is GFP, and the correction sub-factor is:
   intrinsic parameter 1 representing the gene length according to the following equation:

$CF = L(\text{gene of interest})/717$ where L is expressed in number of base pairs,
   intrinsic parameter 2 representing the base composition according to the following equation:

$$CF[\text{base}] = \left( \frac{0.506 * A(g.interst)}{0.34} + \frac{0.063 * T(g.interst)}{0.26} + \frac{0.063 * C(g.interst)}{0.197} + \frac{0.085 * G(g.interst)}{0.203} \right)$$

where A(g. interest) is the percentage of base A in the gene of interest, T(g. interest) is the percentage of base T in the gene of interest, C(g. interest) is the percentage of base C in the gene of interest and G(g. interest) is the percentage of base G in the gene of interest,
   experimental parameter represents the multiplication rate according to the following equation:

$CF[d] = d(\text{gene of interest})/d(gfp)$ where d is the multiplication rate calculated according to the following equation:

$d = \ln(Qf/Qi)/\ln 2$ wherein, Qi and Qf respectively represent the molar quantities of the initial matrix and the products following the PCR.

20. The method according to claim 1, wherein at least one of steps (a), (c) and (d) is performed by a processor.

21. The method according to claim 20, wherein said processor receives data related to:
   the model gene selected
   the mutagenesis technique selected,
   the parameter(s) selected as capable of influencing the mutational load of a gene bank with respect to another to define the correction sub-factors, or
   combinations thereof.

22. The method according to claim 20, wherein said processor calculates:
   the length of the gene of interest,
   the base A composition of the gene of interest,
   the base C composition of the gene of interest,
   the base G composition of the gene of interest,
   the base T composition of the gene of interest,
   the multiplication number of the model gene matrix,
   the multiplication number of the gene of interest matrix, or
   combinations thereof,
wherein the corresponding values are incorporated by the investigator according to the gene of interest and the random mutagenesis result.

23. The method according to claim 20, wherein said processor is any type of multimedia device.

24. The method according to claim 20, wherein said processor integrates the data associated with the charts of the model gene and correction sub-factors.

25. The method of claim 1, wherein one of the at least two intrinsic parameters of a characteristic of gene is its base composition, wherein the correction factor for the base composition is determined by $$CF[\text{base}] = \left( \frac{AMtarg[X] * A(g.interst)}{A(X)} + \frac{TMtarg[X] * T(g.interst)}{T(X)} + \frac{CMtarg[X] * C(g.interst)}{C(X)} + \frac{GMtarg[X] * G(g.interst)}{G(X)} \right),$$

wherein AMtarget[X] is the probability of base A mutating to base T, C, or G in a model gene X; TMtarget[X] is the probability of base T mutating to base A, C, or G in a model gene X; CMtarget[X] is the probability of base C mutating to base A, T, or G in a model gene X; and GMtarget[X] is the probability of base G mutating to base A, T, or C in a model gene X,
   wherein A(g. interest) is the percentage of base A in the gene of interest; T(g. interest) is the percentage of base T in the gene of interest; C(g. interest) is the percentage of base C in the gene of interest; and G(g. interest) is the percentage of base G in the gene of interest, and further
   wherein A(X) is the percentage of base A in the model gene; A(X) is the percentage of base A in the model gene; T(X) is the percentage of base T in the model gene; C(X) is the percentage of base C in the model gene; and G(X) is the percentage of base A in the model gene.

26. The method of claim 25, wherein one of the at least two intrinsic parameters of a characteristic of a gene is its length.

27. A method to determine the mutational load of a gene bank obtained by random mutagenesis of a gene of interest, comprising the following steps:
   a) preparing a chart linking the mutational load (ML) of the gene bank obtained by random mutagenesis of a model gene with the fraction of mutated model genes observed in said bank;
   b) performing, in parallel, random mutagenesis of the model gene used for the preparation of the chart for step (a) and the gene of interest to obtain the corresponding mutated gene banks;

c) determining the mutational load (ML) of the gene bank obtained using the model gene in step (b) on the basis of the chart plotted in step (a); and d) applying a correction factor (CF) to the mutational load (ML) of the mutated model gene bank determined in step (c) to determine the mutational load (ML) in the gene bank of the mutated gene of interest from step (b) wherein the correction factor is determined by $$CF[\text{base}] = \left( \frac{AMtarg[X] * A(g.interst)}{A(X)} + \frac{TMtarg[X] * T(g.interst)}{T(X)} + \frac{CMtarg[X] * C(g.interst)}{C(X)} + \frac{GMtarg[X] * G(g.interst)}{G(X)} \right),$$

wherein Amtarget[X] is the probability of base A mutating to base T, C, or G in a model gene X; Tmtarget[X] is the probability of base T mutating to base A, C, or G in a model gene X; Cmtarget[X] is the probability of base C mutating to base A, T, or G in a model gene X; and Gmtarget[X] is the probability of base G mutating to base A, T, or C in a model gene X, wherein A(g. interest) is the percentage of base A in the gene of interest; T(g. interest) is the percentage of base T in the gene of interest; C(g. interest) is the percentage of base C in the gene of interest; and G(g. interest) is the percentage of base G in the gene of interest, and further wherein A(X) is the percentage of base A in the model gene; A(X) is the percentage of base A in the model gene; T(X) is the percentage of base T in the model gene; C(X) is the percentage of base C in the model gene; and G(X) is the percentage of base A in the model gene.

28. The method of claim 27, wherein the correction factor is also determined by at least one experimental parameter.

29. The method of claim 28, wherein the experimental parameter is the gene multiplication rate during the mutagenesis step.

* * * * *